US00PP23892P2

(12) United States Plant Patent
Isobe

(10) Patent No.: US PP23,892 P2
(45) Date of Patent: Sep. 10, 2013

(54) ***ASARINA* PLANT NAMED 'SUNASAHOWA'**

(50) Latin Name: ***Asarina* hybrid**
Varietal Denomination: Sunasahowa

(75) Inventor: Yasuko Isobe, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 127 days.

(21) Appl. No.: 13/200,534

(22) Filed: Sep. 23, 2011

(51) Int. Cl.
*A01H 5/00* (2006.01)

(52) U.S. Cl.
USPC ..... Plt./263.1

(58) Field of Classification Search
USPC ..... Plt./263.1, 226
See application file for complete search history.

*Primary Examiner* — Howard Locker
(74) *Attorney, Agent, or Firm* — C. A. Whealy

(57) ABSTRACT

A new and distinct cultivar of *Asarina* plant named 'Sunasahowa', characterized by its trailing plant habit; vigorous growth habit; freely branching habit; freely flowering habit; long flowering period; large white-colored flowers; and good garden performance.

1 Drawing Sheet

Botanical designation: *Asarina* hybrid.
Cultivar denomination: 'SUNASAHOWA'.

BACKGROUND OF THE INVENTION

The present invention relates to a new and distinct cultivar of *Asarina* plant, botanically known as *Asarina* hybrid and hereinafter referred to by the name 'Sunasahowa'.

The new *Asarina* plant is a product of a planned breeding program conducted by the Inventor in Higashiomi, Shiga, Japan. The objective of the breeding program is to create new trailing and freely branching *Asarina* plants with attractive leaf and flower coloration.

The new *Asarina* plant originated from a self-pollination in April, 2007 in Higashiomi, Shiga, Japan of a proprietary selection of *Asarina* hybrid identified as code number AS6, not patented. The new *Asarina* plant was discovered and selected by the Inventor as a single flowering plant within the progeny of the stated self-pollination in a controlled greenhouse environment in Higashiomi, Shiga, Japan in December, 2008.

Asexual reproduction of the new *Asarina* plant by vegetative cuttings in a controlled environment in Higashiomi, Shiga, Japan since January, 2009 has shown that the unique features of this new *Asarina* plant are stable and reproduced true to type in successive generations.

SUMMARY OF THE INVENTION

Plants of the new *Asarina* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunasahowa'. These characteristics in combination distinguish 'Sunasahowa' as a new and distinct *Asarina* plant:

1. Trailing plant habit.
2. Vigorous growth habit.
3. Freely branching habit.

4. Freely flowering habit.
5. Long flowering period.
6. Large white-colored flowers.
7. Good garden performance.

Plants of the new *Asarina* can be compared to plants of the parent selection. Plants of the new *Asarina* differ primarily from plants of the parent selection in the following characteristics:

1. Plants of the new *Asarina* have larger flowers than plants of the parent selection.
2. Plants of the new *Asarina* and the parent selection differ in flower color as plants of the parent selection have pink-colored flowers.

Plants of the new *Asarina* can also be compared to plants of *Asarina* hybrid 'Sunasashiro', disclosed in U.S. Plant Pat. No. 19,635. In side-by-side comparisons conducted in Higashiomi, Shiga, Japan, plants of the new Asarina and 'Sunasashiro' differed primarily in the following characteristics:

1. Plants of the new *Asarina* were larger than plants of 'Sunasashiro'.
2. Plants of the new *Asarina* had larger leaves than plants of 'Sunasashiro'.
3. Plants of the new *Asarina* had larger flowers than plants of 'Sunasashiro'.

BRIEF DESCRIPTION OF THE PHOTOGRAPHS

The accompanying colored photographs illustrate the overall appearance of the new *Asarina* plant showing the colors as true as it is reasonably possible to obtain in colored reproductions of this type. Colors in the photographs may differ slightly from the color values cited in the detailed botanical description which accurately describe the colors of the new *Asarina* plant.

The photograph at the top of the sheet comprises a side perspective view of a typical flowering plant of 'Sunasahowa' grown in a hanging basket container.

The photograph at the bottom of the sheet is a close-up view of a typical flowering plant of 'Sunasahowa'.

DETAILED BOTANICAL DESCRIPTION

The aforementioned photographs and following observations, measurements and values describe plants grown during the summer in 18-cm containers in an outdoor nursery Higashiomi, Shiga, Japan and under commercial practices. During the production of the plants, day temperatures averaged 25° C. and night temperatures averaged 18° C. Plants were four months old when the description was taken and five months old when the photographs were taken. In the following description, color references are made to The Royal Horticultural Society Colour Chart, 2001 Edition, except where general terms of ordinary dictionary significance are used.

Botanical classification: *Asarina* hybrid 'Sunasahowa'.

Parentage: Self-pollination of a proprietary selection of *Asarina* hybrid identified as code number AS6, not patented.

Propagation:

*Type*.—By vegetative cuttings.

*Time to initiate roots, summer*.—About ten days at temperatures of 20° C. to 25° C.

*Time to initiate roots, winter*.—About two weeks at temperatures of 15° C. to 20° C.

*Time to produce a rooted young plant, summer*.—About three weeks at temperatures of 20° C. to 25° C.

*Time to produce a rooted young plant, winter*.—About four weeks at temperatures of 15° C. to 20° C.

*Root description*.—Fibrous; white in color.

*Rooting habit*.—Freely branching.

Plant description:

*Plant and growth habit*.—Trailing plant habit; freely branching with lateral branches potentially developing at every node; vigorous growth habit.

Lateral branch description:

*Length*.—About 136 cm.

*Diameter*.—About 2.2 mm.

*Internode length*.—About 3.7 cm.

*Aspect*.—Trailing.

*Texture*.—Pubescent.

*Color*.—Close to 143C.

Foliage description:

*Arrangement*.—Opposite, simple.

*Length*.—About 7.3 cm.

*Width*.—About 6.9 cm.

*Shape*.—Roughly ovate.

*Apex*.—Mucronate.

*Base*.—Cordate.

*Margin*.—Crenate.

*Texture, upper and lower surfaces*.—Pubescent.

*Venation pattern*.—Pinnate; reticulate.

*Color*.—Developing and fully expanded leaves, upper surface: Close to 137A; venation, close to 145B. Developing and fully expanded leaves, lower surface: Close to 137C; venation, close to 145C.

*Petiole*.—Length: About 2.9 cm. Diameter: About 1.8 mm. Texture, upper and lower surfaces: Pubescent. Color, upper and lower surfaces: Close to 145A.

Flower description:

*Flower arrangement and flowering habit*.—Single bilabiate flowers arising from leaf axils; freely flowering habit with numerous flowers developing per plant; flowers face mostly outwardly.

*Fragrance*.—None detected.

*Natural flowering season*.—Early flowering habit, plants of the new Asarina initiate and develop flowers about three to four weeks after planting; long flowering period, flowering commences naturally during the summer and plants flower continuously until late autumn in Japan.

*Flower longevity*.—Individual flowers last about one week on the plant; flowers not persistent.

*Flower buds*.—Length: About 5.3 cm. Diameter: About 1.1 cm. Shape: Cylindrical. Color: Close to 144B.

*Flower diameter*.—About 4.6 cm by 4.8 cm.

*Flower length (depth)*.—About 7.3 cm.

*Throat diameter*.—About 1.6 cm.

*Tube diameter, base*.—About 6 mm.

*Tube length*.—About 5.9 cm.

*Corolla*.—Arrangement: Bilabiate with a two-lobed upper lip and three-lobed lower lip. Length, upper lip: About 1.8 cm. Length, lower lip: About 1.4 cm to 1.6 cm. Width, upper lip: About 2.1 cm. Width, lower lip: About 1.7 cm to 1.9 cm. Shape, upper lip: Two-lobed; apex, rounded. Shape, lower lip: Three-lobed; apex, rounded. Margin, upper and lower lips: Entire, undulate. Texture, upper and lower lips: Smooth, glabrous. Color, upper and lower lips: When opening and fully opened, upper surface: Close to 157D. When opening and fully opened, lower surface: Close to 155B. Color, throat: Close to N155A. Color, tube: Close to 155B.

*Calyx*.—Arrangement: Cup-shaped calyx with five sepals. Sepal length: About 2.1 cm. Sepal width: About 1.4 cm. Sepal shape: Ovate. Sepal apex: Acute. Sepal base: Obtuse. Sepal margin: Entire. Color, upper surface: Close to 143C. Color, lower surface: Close to 145A.

*Peduncles*.—Length: About 2.5 cm. Diameter: About 1.7 mm. Texture: Pubescent. Color: Close to 144B.

*Reproductive organs*.—Stamens: Quantity: Four per flower. Stamen length: About 5 cm. Anther shape: Ellipsoidal. Anther size: About 3.5 mm by 2.5 mm. Anther color: Close to 155A. Pollen amount: Moderate. Pollen color: Close to 155A. Pistils: Quantity: One per flower. Pistil length: About 5.2 cm. Style color: Close to 145D. Stigma shape: Elliptic. Stigma color: Close to 145C. Ovary color: Close to 145D. Seeds and fruits: Seed and fruit development has not been observed on plants of the new *Asarina*.

Garden performance: Plants of the new *Asarina* have been observed to have good garden performance and to tolerate rain, wind and temperatures ranging from about 5° C. to about 35° C.

Pathogen/pest resistance: Plants of the new *Asarina* have not been observed to be resistant to pests and pathogens common to *Asarina* plants.

It is claimed:

1. A new and distinct *Asarina* plant named 'Sunasahowa' as illustrated and described.

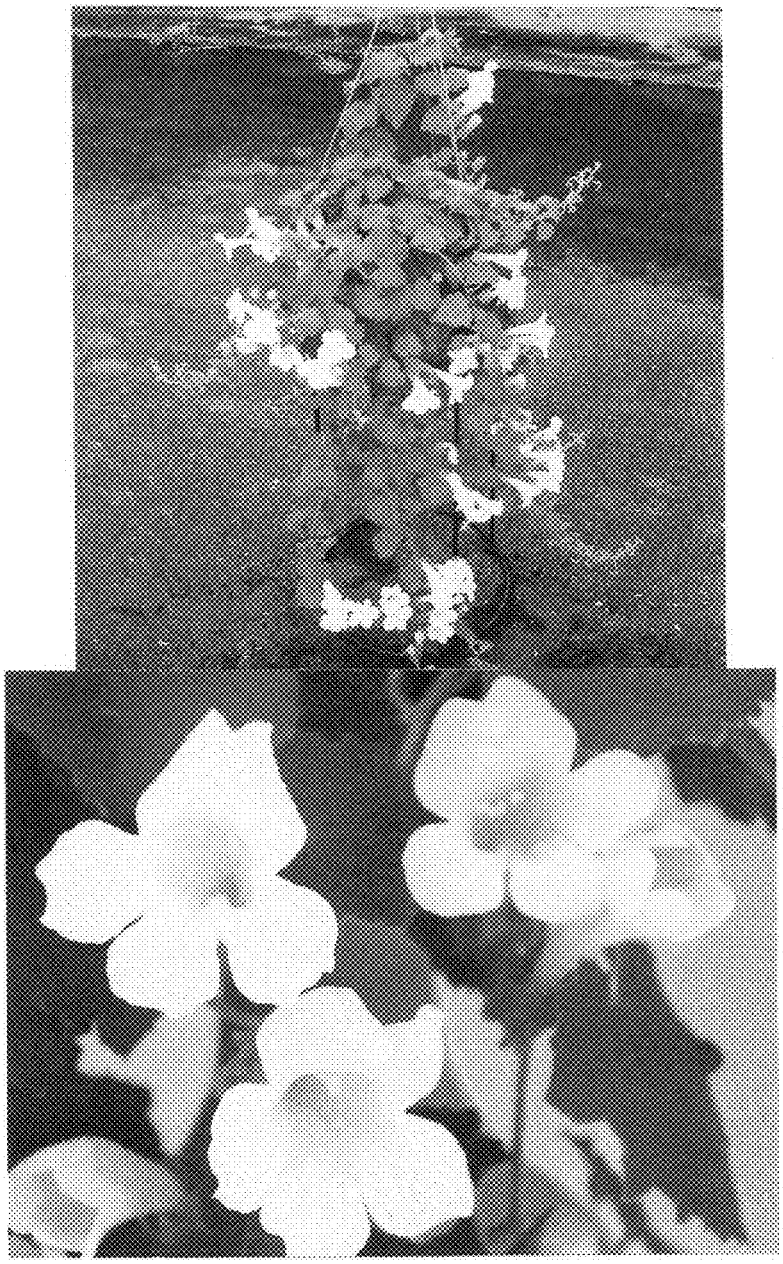

* * * * *